United States Patent [19]

Worst

[11] 4,215,440
[45] Aug. 5, 1980

[54] INTRAOCULAR LENS

[76] Inventor: Jan G. F. Worst, Julia Nalaan 11, Haren, Netherlands

[21] Appl. No.: 945,314

[22] Filed: Sep. 25, 1978

[51] Int. Cl.³ .......................... A61F 1/16; A61F 1/24
[52] U.S. Cl. ....................................................... 3/13
[58] Field of Search ......................................... 3/13, 1

[56] References Cited

U.S. PATENT DOCUMENTS

| | | | |
|---|---|---|---|
| 3,913,148 | 10/1975 | Pottash | 3/13 |
| 3,922,728 | 12/1975 | Krasnov | 3/13 |
| 3,996,626 | 12/1976 | Richards et al. | 3/13 |
| 4,092,743 | 6/1978 | Kelman | 3/13 |
| 4,136,406 | 1/1979 | Norris | 3/13 |

FOREIGN PATENT DOCUMENTS 545352  5/1977  U.S.S.R. .......................................... 3/13

*Primary Examiner*—Ronald L. Frinks
*Attorney, Agent, or Firm*—Joseph Zallen

[57] ABSTRACT

An iris fixation intraocular lens comprising an optical portion and a side support portion comprising a pair of pincer-like extensions for holding a portion of iris tissue.

4 Claims, 7 Drawing Figures

U.S. Patent  Aug. 5, 1980  4,215,440
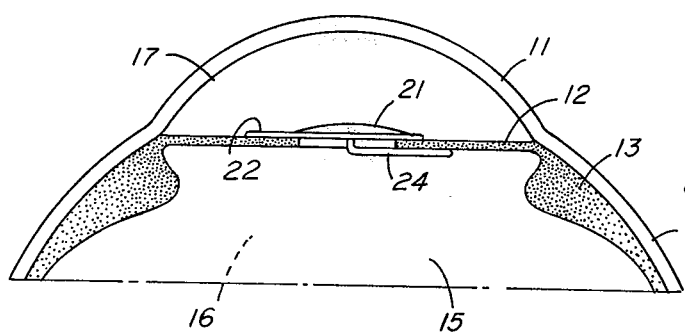
FIG. 1
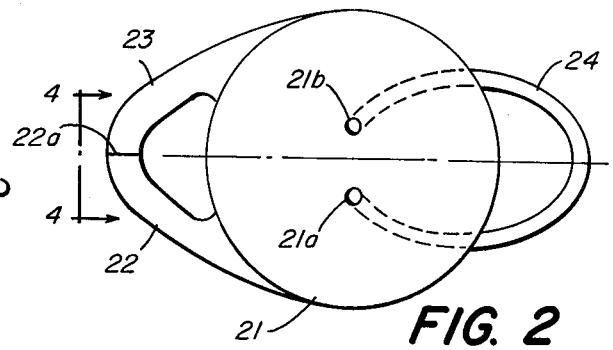
FIG. 3
FIG. 2
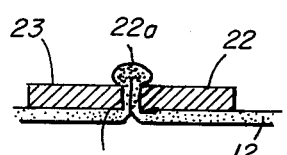
FIG. 4
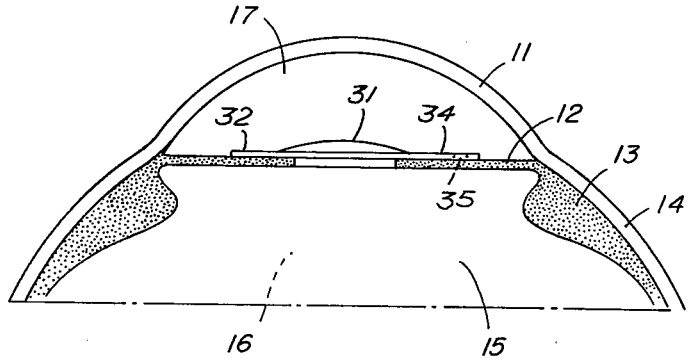
FIG. 5
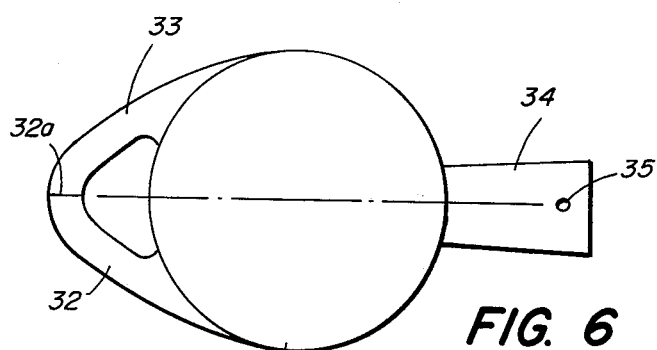
FIG. 6
FIG. 7

INTRAOCULAR LENS

BACKGROUND OF INVENTION

This invention relates to an intraocular lens and in particular to such a lens which is surgically implanted into the eye to substitute for the natural lens.

The natural lens of the eye frequently becomes opaque with age so that vision is severely impaired. This condition of opacity is commonly referred to as cataract. When the opaque natural lens is removed an aphakic correction is needed.

Corrections reported in the prior art have included spectacles, removable contact lenses and surgically implanted intraocular lenses. The choice of which correction to use is a medical decision. However, optically they are different in what they accomplish. Spectacles provide disturbed peripheral vision. A contact lens does provide normal peripheral vision but because it must be removable does not provide the permanence and the precision of optical correction and often is difficult for the older patient to remove or insert. The implanted intraocular lens requires surgery but provides the most precise optical correction including peripheral vision of these three approaches to correction.

The prior art in the field of artificial intraocular lenses is found primarily in Class 3, Sub-class 13 of the United States Patent classification system. Prior art relating to intraocular lenses which are implanted in the anterior chamber of the eye or the chamber in front of the iris include U.S. Pat. Nos. 3,673,616, 3,906,551, 3,922,728, 3,925,825, 3,971,073, 3,979,780, 3,996,626. Prior art patents relating to intraocular lenses in the chamber behind the iris, or the posterior chamber include U.S. Pat. Nos. 3,711,870, 3,866,249, 3,913,148.

In the prior art as exemplified by U.S. Pat. No. 3,906,551 the lens has a support portion which is inserted posteriorly or behind the iris. Fixation of this lens is made with a suture through the less movable portion of the iris.

One object of the present invention is to provide a novel intraocular lens whose entire structure is in the anterior chamber or in front of the iris, but may also be fixated posteriorly.

A further object of this invention is to provide a novel intraocular lens which requires no sutures or capsule fixation.

Other objects and advantages of this invention will be apparent from the description and claims which follow taken together with the appended drawings.

SUMMARY OF INVENTION

The invention comprises broadly an intraocular lens having a first support portion on one side and a second support portion on the other. The first support portion comprises two flexible arms which act as a pair of pincers for an exterior portion of the iris. The second support portion comprises either two similar flexible arms, an elongated portion having a haptic portion registerable with the non-movable portion of the iris at the edge or a loop which will extend through the pupillary aperture and extend posteriorly to the iris but with no suture at all. It is preferred that all varieties of the invention be made of a clinical quality clear plastic such as polymethylmethacrylate.

The pincer portions achieve fixation by grasping some iris tissue and in some cases also grasp the original lens capsule membrane if this capsule is permitted to remain after surgery. In one form of this invention one fixation point is a suture placed through the iris at the upper portion, which ordinarily does not move when the pupil dilates or contracts. This suture is passed around a haptic part in the manner described in U.S. Pat. No. 3,906,551. In another form of the invention one fixation point involves the use of a support loop which goes through the pupil and behind the iris, for capsule fixation. In this latter form of the invention there is no need for a suture and hence less skill is required. In the form of this invention where each support portion comprises flexible pincer arms, there is likewise no need for a suture.

BRIEF DESCRIPTION OF DRAWINGS

FIG. 1 is a sectional view of one embodiment of this invention implanted in an eye.

FIG. 2 is a plan view of the embodiment of this invention illustrated in FIG. 1.

FIG. 3 is an elevation of the embodiment of FIG. 2.

FIG. 4 is an end elevation of the embodiment of FIG. 2. showing the grasping of iris tissue.

FIG. 5 is a cross-sectional view of a second embodiment of this invention shown implanted in the eye.

FIG. 6 is a plan view of the embodiment illustrated in FIG. 5.

FIG. 7 is an elevation of the embodiment of FIG. 5.

SPECIFIC EXAMPLES OF INVENTION

Referring now to FIGS. 1 to 4 there is illustrated therein an embodiment of this invention which comprises an ocular portion 21, a pair of cooperating pincer-like support portions 22 and 23, and a support loop 24 attached to the optical portion at points 21a and 21b. The support loop 24 has short legs 24a extending through the pupillary aperture with the loop 24 extending and contacting the back of the iris 12. The optical portion 21 is situated in front of the pupillary aperture in the aqueous humor of the anterior chamber 17 which is bounded by the cornea 11. The support portion 22, 23 pinches a portion of the iris tissue in the anterior chamber 17 while the loop 24 is in the posterior chamber 15.

The use of this embodiment of the invention provides the surgeon with sufficient flexibility for positioning the lens and also avoids the necessity of a suture by providing the novel pincer-type fixation.

In the form of the invention illustrated in FIGS. 5, 6 and 7 the intraocular lens has an optical portion 31, a pair of cooperating pincer-support arms 32 and 33 and a support extension 34 having an orifice for cooperation with a suturing hole 35 which is positioned on the edge of the iris where substantially no motion takes place during the normal movement of the eye. This particular intraocular lens is noteworthy in that its entire structure is located in the anterior chamber 17 of the eye and the only manipulation with the iris 12 is the formation of the suturing hole 35.

In another form of this invention not illustrated in the drawings, a pair of pincer arms like 22, 23 or 32, 33 replaces loop 24 or extension 34 so that the optical portion (21,31) has a pair of similarly arranged pincer arms on each side as supports.

I claim:

1. An iris fixation intraocular lens comprising an optical portion having a support portion on each side adapted to attach to eye tissue, at least one said side support portion comprising a pair of flat, flexible, normally abutting pincer-like arms adapted to pinch and fixate a portion of one surface only of iris tissue without penetrating to said other surface.

2. An iris fixation intraocular lens comprising an optical portion adapted to be positioned in the anterior chamber of the eye, one side support portion comprising a pair of flat, flexible, normally abutting pincer-like arms adapted to pinch and fixate a portion of the anterior surface only of iris tissue without penetrating to the posterior surface and a second side support portion adapted to attach to eye tissue.

3. An iris fixation intraocular lens comprising an optical portion adapted to be positioned in the anterior chamber of the eye, one side support portion comprising a pair of flat, flexible, normally abutting pincer-like arms adapted to pinch and fixate a portion of the anterior surface only of iris tissue without penetrating said tissue to the posterior surface and a second side support portion which is an extension having an orifice adapted for suturing to the relatively non-movable portion of the iris; said lens being characterised in that its entire structure is adapted to be spaced completely within the anterior chamber of the eye.

4. An iris fixation intraocular lens comprising an optical portion adapted to be positioned within the anterior chamber of the eye, one side support portion comprising a pair of flat, flexible, normally abutting pincer-like arms adapted to pinch and fixate a portion of the anterior surface only of iris tissue without penetrating to the posterior surface and a second side support portion which has a loop adapted to extend to the pupillary aperture so as to be positionable posteriorly to the iris.

* * * * *